United States Patent

Cole et al.

Patent Number: 5,723,798
Date of Patent: Mar. 3, 1998

[54] MEASURING AND CONTROLLING PANEL SINGULATION SHOCK

[75] Inventors: Michael Paul Cole, Mission; David Paul Bellus, McAllen, both of Tex.

[73] Assignee: Delco Electronics Corporation, Kokomo, Ind.

[21] Appl. No.: 734,059

[22] Filed: Oct. 18, 1996

[51] Int. Cl.⁶ ............................................. G01N 19/00
[52] U.S. Cl. .................... 73/865.9; 29/829; 29/830; 73/801; 73/587
[58] Field of Search ............................. 73/865.9, 851, 73/801, 812, 587; 83/929.1, 76.8; 29/829, 846, 847, 412, 414, 417

[56] References Cited

U.S. PATENT DOCUMENTS

| | | |
|---|---|---|
| 4,208,895 | 6/1980 | Grigorenko et al. .................... 72/8 |
| 4,633,720 | 1/1987 | Dybel et al. .................... 73/862.53 |
| 4,791,721 | 12/1988 | Anderson et al. .................... 29/829 |
| 4,901,575 | 2/1990 | Bohannan et al. .................... 73/587 |
| 5,184,517 | 2/1993 | Kelzer .................... 73/851 |

Primary Examiner—Hezron E. Williams
Assistant Examiner—Nashmiya Ashraf
Attorney, Agent, or Firm—Jimmy L. Funke

[57] ABSTRACT

A panel of several circuit boards connected by bridges is separated into individual boards by opposed dies which sever the link. Shock from the die impact can damage fragile components mounted on the circuit boards, especially when dies become dull and the singulation machine needs to be serviced. Periodic measurements of die acceleration and panel acceleration are made during a die wear cycle to obtain an empirical function of the correlation of those parameters. A threshold of acceptable panel acceleration is established and the related limit of die acceleration is determined from the correlation function. Die acceleration is then monitored during a production run to predict when machine servicing is needed.

9 Claims, 1 Drawing Sheet

MEASURING AND CONTROLLING PANEL SINGULATION SHOCK

FIELD OF THE INVENTION

This invention relates to the separation of a panel into smaller panels such as printed circuit boards and particularly a method of measuring an controlling the shock during such separation.

BACKGROUND OF THE INVENTION

Mass production of printed electronic circuits has promoted the manufacture of several connected circuit boards at once to facilitate handling and to decrease processing time. The panels are often preformed by cutting along boundaries but leaving connecting bridges between individual boards. These connected circuit boards typically have surface mount and stick lead components assembled to them and are then broken or cut into individual circuit boards. The process of separating the circuit boards is called singulation or depaneling. One technology used to singulate circuit boards involves using opposing dies that hold the board in position while cutting edges in the die come together to shear bridges between the joined circuit boards. The opposing die technology is illustrated by the U.S. Pat. No. 4,791,721 to Anderson et al. entitled "SINGULATION SYSTEM FOR PRINTED CIRCUIT BOARDS". There, a panel is inserted between a fixed lower die and a movable upper die carrying perforators or punches which sever the bridges on the panel when the dies close.

The shearing process imparts high forces to the circuit board which are absorbed in the board as potential energy. Once the cutting edges pass through the board bridges, that potential energy is released as kinetic energy in the form of high frequency vibrations or shock. These high frequency vibrations have high accelerations which are transmitted through the board to the components. Excessive acceleration will damage or destroy the mounted components. The management of the transmitted shock is critical to the quality of singulated circuit board components. Initially setting up a singulation process for acceptable shock levels does not ensure continued operation at that level because of operational changes due to die wear, machine lubrication, press force variation and other variables. If the machine is not serviced at appropriate times its performance will deteriorate to yield unacceptable products. It is desirable then to know when the machine is approaching its limit of acceptable performance to enable timely machine service.

SUMMARY OF THE INVENTION

It is therefore an object of the invention to control the shock or acceleration in circuit boards during singulation to a level which does not damage circuit components. Another object is to use a measurement of die acceleration and its correlation to circuit board acceleration to control the level of shock. An additional object is to use such measurement to monitor continued machine operation in mass production environments to ensure that shock remains at an acceptable level. Still another object is to provide automated statistical process control for opposing die singulation to prevent damaged components due to shock.

To carry out the invention for a particular application, acceleration tests are made on a sufficient number of panels at various die accelerations for a statistically significant correlation. For such tests an accelerometer is fixed to a die, preferably at the point of highest acceleration, to measure die acceleration, and an accelerometer is fixed to the panel to measure panel acceleration. An empirical function of the correlation of die and panel accelerations is then obtained and an acceptable range or limit value of die acceleration corresponding to acceptable panel acceleration is identified. During production runs, the die is still equipped with an accelerometer and the acceleration is measured and compared with the acceptable range or limit to determine whether the panel singulation machine is performing within proper bounds. When an out-of-limit acceleration is approached a message is transmitted to the machine operator indicating the machine status. This allows the operators to make timely corrections so that performance does not deteriorate enough to yield rejected products.

BRIEF DESCRIPTION OF THE DRAWINGS

The above and other advantages of the invention will become more apparent from the following description taken in conjunction with the accompanying drawings wherein like references refer to like parts and wherein.

DESCRIPTION OF THE INVENTION

The ensuing description is directed to the singulation of circuit board panels carrying fragile components which are subject to damage by the shock of singulation; the invention is applicable, however to other products which are sensitive to the singulation process.

Figure 1:
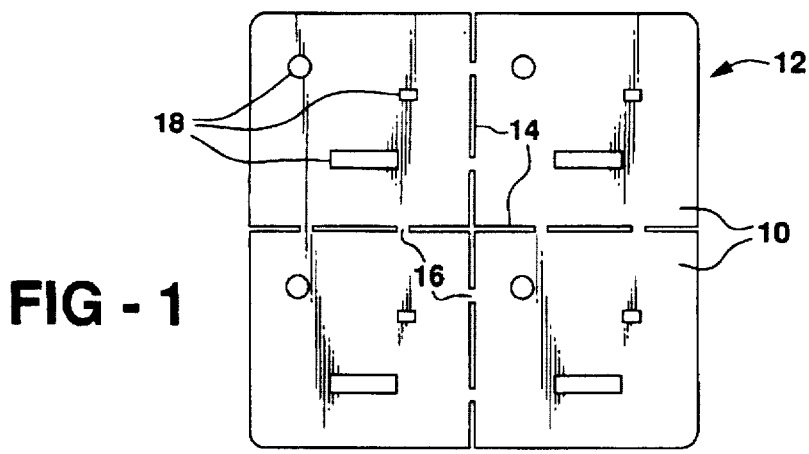
FIG. 1 is a top view of a panel comprising a plurality of joined circuit boards.

Referring to FIG. 1, a group of printed circuit boards 10 are defined in a panel 12 by cuts or slots 14 along adjoining boundaries. Each board is joined to its neighbor by bridges 16 crossing the boundaries. The panel is processed to apply electronic components 18 on each circuit board 10. The components include surface mount and stick lead types and include some which may be fragile such as ceramic resistors and capacitors, diodes, lamps, solder joints and displays. After the components are applied, the panel is singulated or separated into individual circuit boards. It is, of course, important that the none of the components be damaged by the singulation.

Figure 2:
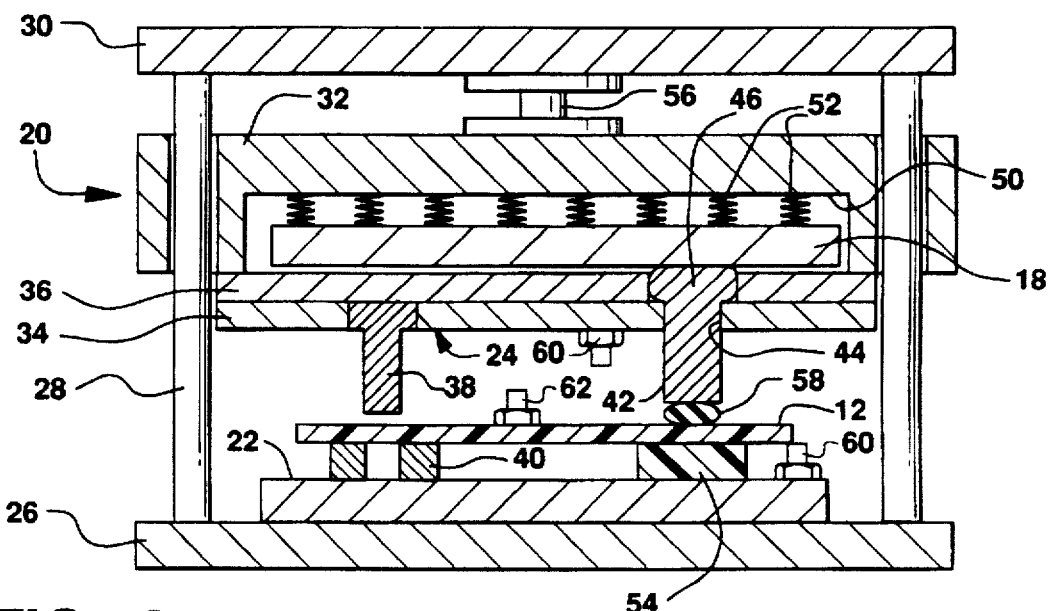
FIG. 2 is a schematic diagram of a panel singulation apparatus in cross section equipped to carry out the method of the invention.

FIG. 2 shows a singulation apparatus which comprises a press 20 containing a fixed die 22 (which can actually slide horizontally for loading and unloading parts) and a movable die 24. The press 20 includes a base 26, a post 28 at each corner of the base 26, a top restraining plate 30 and a top table 32 slidably mounted on the posts. The movable die includes a punch pad 34 and a back up plate 36 which are attached to the top table for movement with the table. A punch or perforator 38 (one corresponding to each of the bridges 16) depends from the punch pad 34 and is aligned with an annular bushing 40 supported on the fixed die. Each of a number of hold down pins 42 is slidably mounted in apertures 44 in the punch pad 34 and back up plate 36 and has a head 46 bearing on a spring loaded plate 48 which is mounted within a counter bore 50 in the top table 32 and biased downward by springs 52. A back up pad 54 on the fixed die 22 is aligned with each hold down pin. A cylinder 56 between the top restraining plate 30 and the top table 32 affords the motive force to move the die 24 up and down. As thus far described, the apparatus is like that described in the above mentioned U.S. Pat. No. 4,791,721 to Anderson et al. In addition, however, it is desired to include a rubber-like damping member 58 on the bottom of each hold down pin 42 for contact with the panel 12.

In operation, a panel 12 is placed between the dies 22 and 24 with the bridges 16 aligned with the perforators, the top table is moved down to first urge the hold down pins 42 against the panel to hold it against the back up pads 54, and then to push the perforators 38 through the panel to sever the bridges 16. The action of the opposed dies 22 and 24 not only severs the bridges but the perforators 38 impact the panel 12 to send high frequency vibrations through the panel to the components. The damping members 58 help absorb the vibrational energy imparted to the panel to reduce the vibration and thus the acceleration transmitted to the components. To further reduce the acceleration of the panel and its effect on the components, the machine is initially set up with sharpened perforators, well lubricated posts, and properly adjusted approach velocity (of the die 24 toward the panel) to minimize the panel acceleration. However, in the course of mass production usage over many days or weeks, the die wear and other machine changes cause the panel acceleration and the effect on the components to gradually increase to the point where damage is occurring. Then the machine must be serviced to improve the performance. Thus the machine by its nature is subject to cycles of wear and corrective maintenance. It is desirable to know when to perform the maintenance to prevent operation which causes component damage and yet avoid undue frequency of maintenance.

To predict the time when service is required, the acceleration of the die and of the panel is correlated, a limit value of die acceleration is established based on the tolerance of the board components to panel acceleration, and the die acceleration is monitored during production runs to detect the approach of die acceleration to the limit value. Then die sharpening and other machine maintenance is scheduled before the limit value is exceeding, thereby keeping the stress on the components to a safe level.

For a given die set, accelerometers 60 are attached to various places on the dies and the machine is operated to determine the location of highest die acceleration. The preferred location may be on either die or both of them. Similarly, an accelerometer 62 is attached to various places on the panel and the machine is operated to determine the location of highest panel acceleration. Alternatively, the panel location of a fragile component may be used as an accelerometer site.

Figure 3:
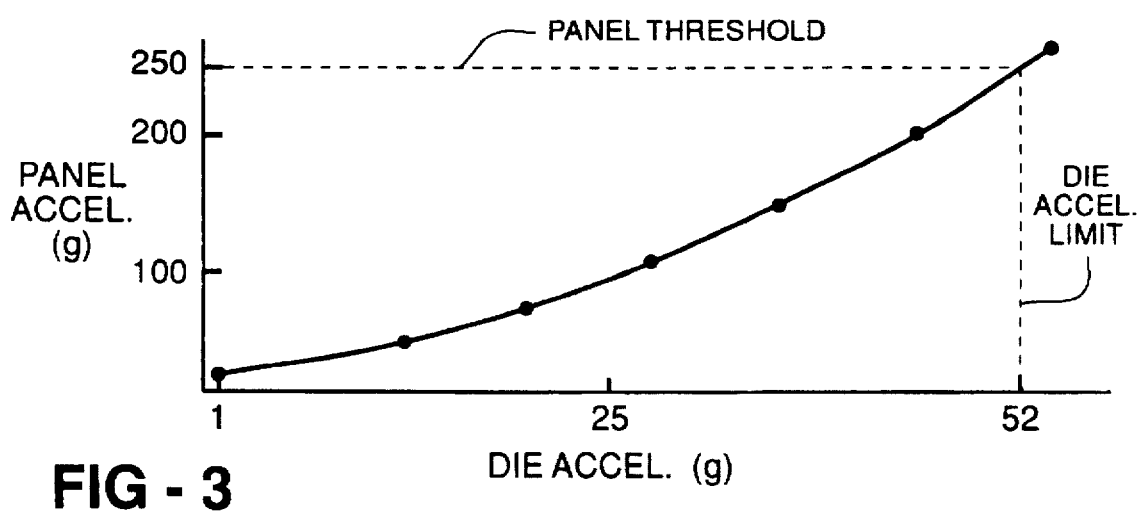
FIG. 3 is a graph of die acceleration vs. panel acceleration illustrating the method of the invention.

Next, a statistically significant number of die and panel accelerations are measured at several intervals during the die wear cycle to establish a correlation between die and panel accelerations. To carry out these measurements, an accelerometer 60 is attached by adhesive to a die location of highest acceleration and a plurality of panels are similarly instrumented with accelerometers 62 either at high acceleration sites or at fragile component sites. At the beginning of a production run when the machine has been serviced and the die sharpened, several instrumented panels are processed in the machine and the die and panel accelerations are measured for each panel. Each set of these accelerations are averaged to obtain the correlation for one point. After a production run of 1000 panels, for example, several more instrumented panels are processed to obtain another correlation point. This procedure is continued through the die wear cycle at several intervals and enough points are accumulated to establish an empirical curve representing the correlation function between die and panel accelerations as illustrated in FIG. 3. Then, on the basis of experience with the onset of damaged components, a panel acceleration threshold is established and the corresponding die acceleration limit is determined from the correlation function. The correlation function may be used in the graphical form or, if desired, an equation can be fit to the curve for use in calculating the required limits.

After the empirical determination of the acceleration limit, the accelerometer 60 is used on the die during production runs of the machine. The die acceleration is monitored and compared to the die acceleration limit. The wear of the die and other deterioration of press condition is thus tracked during production and as the die acceleration approaches the limit, perhaps two days before the limit is reached, machine maintenance is scheduled, thereby ensuring that the perforators are sharpened and other service is completed before damaged components result from the singulation process.

It will thus be seen that the singulation of panels into individual circuit boards is improved by ensuring that fragile components on the panel will not be damaged due to excessive shock produced by the singulation apparatus. At the same time optimum preventative maintenance schedules can be formulated by observing the continuous die acceleration data.

The embodiments of the invention in which an exclusive property or priviledge is claimed are defined as follows:

1. A method of controlling panel shock during singulation by apparatus including opposed dies, the apparatus being subject to cycles of wear and corrective maintenance, comprising the steps of:

measuring die acceleration of at least one die and panel acceleration during a statistically significant number of tests of panel singulation at spaced intervals in a wear cycle;

correlating the die and panel acceleration measurements;

determining a range of panel acceleration related to acceptable levels of shock and a range of corresponding acceptable die acceleration; and thereafter controlling shock by measuring die acceleration of the at least one die during panel singulation, and maintaining the apparatus to keep the die acceleration measurements within the determined range of acceptable die acceleration.

2. The method as defined in claim 1 wherein the opposed dies include a fixed die and a movable die, and wherein:

the step of measuring die acceleration and panel acceleration includes fixing an accelerometer on the at least one die and fixing another accelerometer on the panel.

3. The method as defined in claim 1 wherein the opposed dies include a fixed die and a movable die, and wherein the step of measuring die acceleration includes:

determining the highest acceleration point on the movable die; and fixing an accelerometer on the movable die substantially at the highest acceleration point.

4. The method as defined in claim 1 wherein the step of measuring panel acceleration includes:

determining the highest acceleration point on the panel; and fixing an accelerometer on the panel substantially at the highest acceleration point.

5. The method as defined in claim 1 wherein the step of measuring panel acceleration includes:

identifying a panel location for mounting a fragile component; and fixing an accelerometer on the panel substantially at the identified panel location.

6. The method as defined in claim 1 wherein the step of correlating the die and panel acceleration measurements comprises:

performing a statistically significant number of die acceleration and panel acceleration measurements at each interval and averaging the measurements to define a point for each interval; and determining a die and panel acceleration correlation from the defined points.

7. The method as defined in claim 6 wherein the step of determining a correlation comprises calculating the equation of an empirical function that passes through the defined points.

8. The method as defined in claim 6 wherein the step of determining a correlation comprises plotting a curve that passes through the defined points.

9. The method as defined in claim 1 wherein the step of controlling shocks include:

issuing a maintenance message when the die acceleration approaches a limit of the range of acceptable die acceleration.

* * * * *